US012385021B2

(12) United States Patent
Jiang et al.

(10) Patent No.: US 12,385,021 B2
(45) Date of Patent: Aug. 12, 2025

(54) HEAT-RESISTANT DNA POLYMERASE MUTANT WITH HIGH AMPLIFICATION ACTIVITY

(71) Applicant: Daan Gene Co., Ltd., Guangdong (CN)

(72) Inventors: Xiwen Jiang, Guangdong (CN); Aishan Liu, Guangdong (CN)

(73) Assignee: DAAN GENE CO., LTD., Guangdong (CN)

( * ) Notice: Subject to any disclaimer, the term of this patent is extended or adjusted under 35 U.S.C. 154(b) by 944 days.

(21) Appl. No.: 16/957,276

(22) PCT Filed: Apr. 30, 2020

(86) PCT No.: PCT/CN2020/088341
§ 371 (c)(1),
(2) Date: Jun. 23, 2020

(87) PCT Pub. No.: WO2021/217597
PCT Pub. Date: Nov. 4, 2021

(65) Prior Publication Data
US 2022/0325259 A1    Oct. 13, 2022

(51) Int. Cl.
*C12N 9/12* (2006.01)

(52) U.S. Cl.
CPC .... *C12N 9/1252* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 9,523,085 B2 * | 12/2016 | Hogrefe | C12N 9/1252 |
| 2005/0112637 A1 * | 5/2005 | Chatterjee | C12N 9/1252 |
| | | | 435/6.12 |
| 2019/0225951 A1 | 7/2019 | Meng et al. | |

FOREIGN PATENT DOCUMENTS

| | | |
|---|---|---|
| CN | 101528919 A | 9/2009 |
| CN | 107475216 A | 12/2017 |
| CN | 109486788 A | 3/2019 |
| CN | 109957557 A | 7/2019 |
| CN | 111032863 A | 4/2020 |
| WO | 2009010251 A2 | 1/2009 |
| WO | 2011014885 A1 | 2/2011 |
| WO | WO-2012097318 A2 * | 7/2012 ........... C12N 9/1252 |
| WO | 2016183294 A1 | 11/2016 |

OTHER PUBLICATIONS

Suzuki et al., Proc. Natl. Acad. Sci. USA, vol. 93, pp. 9670-9675, Sep. 1996.*
Ngo et al. in The Protein Folding Problem and Tertiary Structure Prediction, 1994, Merz et al. (ed.), Birkhauser, Boston, MA, pp. 433 and 492-495.*
Wang et al., "A novel strategy to engineer DNA polymerases for enhanced processivity and improved performance in vitro", Nucleic Acids Research, vol. 32, No. 3, Published online Feb. 18, 2004, pp. 1197-1207.
Suzuki et al., "Thermus Aquaticus DNA Polymerase I Mutants With Altered Fidelity. Interacting Mutations in the O-helix", The Journal of Biological Chemistry, vol. 275, No. 42, Oct. 20, 2000, pp. 32728-32735.
Yamagami et al., "Mutant Taq DNA polymerases with improved elongation ability as a useful reagent for genetic engineering", Frontiers in Microbiology, Sep. 3, 2014, vol. 5, Article 461, 11 pages provided.
Zhang et al., "Direct DNA Amplification From Crude Clinical Samples Using a PCR Enhancer Cocktail and Novel Mutants of Taq", Journal of Molecular Diagnostics, vol. 12, No. 2, Mar. 2010, 10 pages.
Vainshtein et al., "Peptide rescue of an N-terminal truncation of the Stoffel fragment of taq DNA polymerase", Protein Science, accepted Jun. 25, 1996, pp. 1785-1792.
International Search Report (with English translation) and Written Opinion issued in PCT/CN2020/088341, dated Jan. 27, 2021, 13 pages provided.
The extended European search report issued in European Application No. 20761492.6, dated Feb. 17, 2022, 9 pages provided.
RecName: Full=DNA polymerase I, thermostable ; AltName: Full= Taq polymerase 1, GenBank, created Feb. 1, 1991, 6 pages, cited in ISR.
Yamagami et al., "Mutant Taq DNA polymerases with improved elongation ability as a useful reagent for genetic engineering", Frontiers in Microbiology, vol. 5 Issue No. SEP, published 2014, 10 pages, cited in EESR.
Arezi et al., "Compartmentalized self-replication under fast PCR cycling conditions yields Taq DNA polymerase mutants with increased DNA-binding affinity and blood resistance", Frontiers in Microbiology, Published Aug. 14, 2014, 10 pages, cited in EESR.

* cited by examiner

*Primary Examiner* — Richard G Hutson
(74) *Attorney, Agent, or Firm* — HSML P.C.

(57) ABSTRACT

The present invention provides a heat-resistant DNA polymerase mutant with high amplification activity. Particularly, the present invention uses protein directed evolution technology to construct a random mutation library for the polymerase active domain of Taq enzyme, and gradually adds screening pressure, so that unsuitable mutations will be eliminated naturally, and mutations with dominant traits will gradually accumulate. Finally, a series of amino acid sites and their mutations that are critical to Taq enzyme amplification and polymerization performance will be selected, and a Taq enzyme mutant with high amplification activity will be obtained.

3 Claims, No Drawings
Specification includes a Sequence Listing.

SEQUENCE LISTING

```
<160> NUMBER OF SEQ ID NOS: 12

<210> SEQ ID NO 1
<211> LENGTH: 2496
<212> TYPE: DNA
<213> ORGANISM: Artificial sequence
<220> FEATURE:
<223> OTHER INFORMATION: Polynucleotide

<400> SEQUENCE: 1
atgcgtggca tgctgccgct tttcgagcct aagggacgcg ttcttcttgt ggatggacat      60
catctggcgt accgtacctt tcatgccctg aagggcctga ccacttcgcg tggggaaccc     120
gtgcaagcag tttatggatt cgccaaatcg ttacttaagg ctctgaagga ggatggtgat     180
gcggtcattg ttgtgttcga cgcaaaagct ccctcgttcc gtcacgaggc ctacgcggc      240 tataaagctg ggcgtgcacc cacacctgag gattttcccc ggcaacttgc tttgataaag     300
gaattagtag acctgttagg cctggcgcgg ttagaagtgc cgggttacga agcagatgac     360
gtcttggcta gtttagcgaa aaaggctgaa aagagggat atgaagtgcg gatcctgacc      420
gcggataaag atctgtatca actgttgtcc gaccgtattc acgtgcttca tccggagggc     480
tacttgataa ccccggcttg gctgtgggag aaatatgggc tgcgtccaga tcagtgggct     540
gattatcgtg cacttacagg cgatgaatct gataatcttc ccggcgtcaa ggggattggt     600
gagaaaaccg cccgtaaact tttggaggag tggggcagct tggaggcgct gttgaagaat     660
```

```
ctggatcgtt tgaaacccgc tatacgggaa aaatcttgg cgcacatgga cgacttaaaa    720
ctgtcttggg acctggcgaa agttcgtact gatttgccgc tggaggtcga ctttgcgaag    780
cgtcgcgagc ccgatcgtga acgtcttcgc gcatttctgg agcgtttaga atttggctcc    840
ctgttgcatg agtttggttt gcttgaaagc ccgaaggcac ttgaggaagc tccttggcct    900
ccgcctgagg gcgcttttgt cggatttgtc ttgagccgta agaaccgat gtgggcggac     960 ttactggccc ttgctgctgc tcgtgggggt cgcgtgcatc gcgcaccgga gccatacaaa   1020
gcacttcgtg accttaaaga agcccgtggc ttgttggcaa agatttaag tgtcctggct    1080 ttacgcgagg gcttgggctt accaccggga gatgatccga tgcttttggc ctatctgctg   1140
gacccgagca acacgactcc agagggcgtt gcccgtcgtt atggcggaga atggacggag   1200
gaggcgggag agcgcgcagc gttaagcgag cgtctgtttg ctaatctgtg gggacgctta   1260
gagggagagg agcgcctgtt gtggttgtac cgtgaagtgg aacggccgct gagtgcagtg   1320
ttagctcaca tggaagcaac cggggtgcgg ctggacgttg cgtatttgcg tgcgctgtcg   1380
ttagaggtcg cggaggaaat agcccgtctg gaggccgaag tattccgttt ggctggccat   1440
cctttcaacc tgaacagtcg ggatcagctg gaacgtgtac tttttgatga actggggctg   1500
cccgccatcg gcaaaaccga aaaaaccggc aaacgtagca cctctgcggc agtgctggaa   1560
gcgttacgtg aagctcatcc gattgtggag aaaattctgc aatatcgcga attgacgaaa   1620
ctgaagagca cctatattga tccgctgcca gacttaattc accccgtac cggacggttg    1680 catacccgct tcaaccagac cgcgacgcg acagggcggc tgagtagcag cgatccgaac    1740
ctgcaaaaca ttcccgtgcg tacccgctg ggtcagcgta ttcgccgtgc tttcattgcc    1800
gaggaaggct ggctgctggt cgcgctggac tactcgcaaa tcgaattgcg tgtgttggcc   1860
cacctgtcgg gcgacgaaaa cttaatacgc gtgttcaag aaggtcgtga catacatact    1920
gaaaccgcgt cctggatgtt tggagtccca cgggaggctg tcgatcctct tatgcgtcgt   1980
gccgccaaaa caattaactt cggagttctg tacggcatgt cggcacatcg tttatcacag   2040
gaactggcga ttccgtatga agaagcgcag gccttcatag aacgttattt ccaatcattc    2100
cccaaggtgc gggcctggat tgagaagacc ctggaagagg gccgtcgtcg tggctatgta   2160
gagactctgt tcggacgtcg gcggtatgta cccgatcttg aggcccgtgt gaagtccgtt   2220
cgtgaggcag cagaacgtat ggcgtttaac atgccagtcc agggcacagc ggcggacctg   2280
atgaaattag ctatggttaa gctgtttccg cgtttggaag aaatgggcgc tcgtatgctg   2340
ttacaggttc atgacgagtt agtattagaa gcaccgaagg agcgtgccga agccgtggcc   2400
cggttagcca agaggtaat ggaaggcgtc taccccttg cagtcccgct tgaagtcgaa     2460
gttggcatag gggaagactg gttatctgcg aaggaa                             2496
```

<210> SEQ ID NO 2
<211> LENGTH: 832
<212> TYPE: PRT
<213> ORGANISM: Artificial sequence
<220> FEATURE:
<223> OTHER INFORMATION: Polypeptide

<400> SEQUENCE: 2

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30
```

```
Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
                100                 105                 110

Val Pro Gly Tyr Glu Ala Asp Asp Val Leu Ala Ser Leu Ala Lys Lys
             115                 120                 125

Ala Glu Lys Glu Gly Tyr Glu Val Arg Ile Leu Thr Ala Asp Lys Asp
         130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
             180                 185                 190

Leu Pro Gly Val Lys Gly Ile Gly Glu Lys Thr Ala Arg Lys Leu Leu
         195                 200                 205

Glu Glu Trp Gly Ser Leu Glu Ala Leu Leu Lys Asn Leu Asp Arg Leu
     210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
             260                 265                 270

Leu Glu Arg Leu Glu Phe Gly Ser Leu Leu His Glu Phe Gly Leu Leu
         275                 280                 285

Glu Ser Pro Lys Ala Leu Glu Glu Ala Pro Trp Pro Pro Pro Glu Gly
     290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
             340                 345                 350

Ala Lys Asp Leu Ser Val Leu Ala Leu Arg Glu Gly Leu Gly Leu Pro
         355                 360                 365

Pro Gly Asp Asp Pro Met Leu Leu Ala Tyr Leu Leu Asp Pro Ser Asn
     370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
             420                 425                 430

Val Glu Arg Pro Leu Ser Ala Val Leu Ala His Met Glu Ala Thr Gly
         435                 440                 445

Val Arg Leu Asp Val Ala Tyr Leu Arg Ala Leu Ser Leu Glu Val Ala
```

```
                    450                 455                 460
Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
        530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 1269
<212> TYPE: DNA
<213> ORGANISM: Artificial sequence
<220> FEATURE:
<223> OTHER INFORMATION: Polynucleotide
```

<400> SEQUENCE: 3

```
atgcgtggca tgctgccgct tttcgagcct aagggacgcg ttcttcttgt ggatggacat      60
catctggcgt accgtacctt tcatgccctg aagggcctga ccacttcgcg tggggaaccc     120
gtgcaagcag tttatggatt cgccaaatcg ttacttaagg ctctgaagga ggatggtgat     180
gcggtcattg ttgtgttcga cgcaaaagct ccctcgttcc gtcacgaggc ctacggcggc     240
tataaagctg ggcgtgcacc cacacctgag gattttcccc ggcaacttgc tttgataaag     300
gaattagtag acctgttagg cctggcgcgg ttagaagtgc cgggttacga agcagatgac     360
gtcttggcta gtttagcgaa aaaggctgaa aagagggat atgaagtgcg gatcctgacc     420
gcggataaag atctgtatca actgttgtcc gaccgtattc acgtgcttca tccggagggc     480
tacttgataa ccccggcttg gctgtgggag aaatatgggc tgcgtccaga tcagtgggct     540
gattatcgtg cacttacagg cgatgaatct gataatcttc ccggcgtcaa ggggattggt     600
gagaaaaccg cccgtaaact tttggaggag tggggcagct tggaggcgct gttgaagaat     660
ctggatcgtt tgaaaccgc tatacgggaa aaaatcttgg cgcacatgga cgacttaaaa     720
ctgtcttggg acctggcgaa agttcgtact gatttgccgc tggaggtcga ctttgcgaag     780
cgtcgcgagc ccgatcgtga acgtcttcgc gcatttctgg agcgtttaga atttggctcc     840
ctgttgcatg agtttggttt gcttgaaagc ccgaaggcac ttgaggaagc tccttggcct     900
ccgcctgagg gcgcttttgt cggatttgtc ttgagccgta agaaccgat gtgggcggac     960
ttactggccc ttgctgctgc tcgtgggggt cgcgtgcatc gcgcaccgga gccatacaaa    1020
gcacttcgtg accttaaaga agcccgtggc ttgttggcaa aagatttaag tgtcctggct    1080
ttacgcgagg gcttgggctt accaccggga gatgatccga tgcttttggc ctatctgctg    1140
gacccgagca acacgactcc agagggcgtt gcccgtcgtt atggcggaga atggacggag    1200
gaggcgggag agcgcgcagc gttaagcgag cgtctgtttg ctaatctgtg ggacgctta     1260
gagggagag                                                             1269
```

<210> SEQ ID NO 4
<211> LENGTH: 30
<212> TYPE: DNA
<213> ORGANISM: Artificial sequence
<220> FEATURE:
<223> OTHER INFORMATION: Primer

<400> SEQUENCE: 4

```
atatcatatg cgtggcatgc tgccgctttt                                        30
```

<210> SEQ ID NO 5
<211> LENGTH: 30
<212> TYPE: DNA
<213> ORGANISM: Artificial sequence
<220> FEATURE:
<223> OTHER INFORMATION: Primer

<400> SEQUENCE: 5

```
gcatgaattc cgtctcctct ccctctaagc                                        30
```

<210> SEQ ID NO 6
<211> LENGTH: 1236
<212> TYPE: DNA
<213> ORGANISM: Artificial sequence
<220> FEATURE:
<223> OTHER INFORMATION: Polynucleotide

<400> SEQUENCE: 6

```
ggagaggagc gcctgttgtg gttgtaccgt gaagtggaac ggccgctgag tgcagtgtta      60
gctcacatgg aagcaaccgg ggtgcggctg gacgttgcgt atttgcgtgc gctgtcgtta     120
gaggtcgcgg aggaaatagc ccgtctggag gccgaagtat tccgtttggc tggccatcct     180
ttcaacctga acagtcggga tcagctggaa cgtgtacttt ttgatgaact ggggctgccc     240
gccatcggca aaccgaaaa aaccggcaaa cgtagcacct ctgcggcagt gctggaagcg     300
ttacgtgaag ctcatccgat tgtggagaaa attctgcaat atcgcgaatt gacgaaactg     360
aagagcacct atattgatcc gctgccagac ttaattcacc cccgtaccgg acggttgcat     420
acccgcttca accagaccgc gacggcgaca gggcggctga gtagcagcga tccgaacctg     480
caaaacattc ccgtgcgtac cccgctgggt cagcgtattc gccgtgcttt cattgccgag     540
gaaggctggt gctggtcgc gctggactac tcgcaaatcg aattgcgtgt gttggcccac     600
ctgtcgggcg acgaaaactt aatacgcgtg tttcaagaag gtcgtgacat acatactgaa     660
accgcgtcct ggatgtttgg agtcccacgg gaggctgtcg atcctcttat gcgtcgtgcc     720
gccaaaacaa ttaacttcgg agttctgtac ggcatgtcgg cacatcgttt atcacaggaa     780
ctggcgattc cgtatgaaga agcgcaggcc ttcatagaac gttatttcca atcattcccc     840
aaggtgcggg cctggattga aagaccctg gaagagggcc gtcgtcgtgg ctatgtagag     900
actctgttcg gacgtcggcg gtatgtaccc gatcttgagg cccgtgtgaa gtccgttcgt     960
gaggcagcag aacgtatggc gtttaacatg ccagtccagg gcacagcggc ggacctgatg    1020
aaattagcta tggttaagct gttttccgcgt ttggaagaaa tgggcgctcg tatgctgtta    1080
caggttcatg acgagttagt attagaagca ccgaaggagc gtgccgaagc cgtggcccgg    1140
ttagccaaag aggtaatgga aggcgtctac cccccttgcag tcccgcttga agtcgaagtt    1200
ggcatagggg aagactggtt atctgcgaag gaataa                             1236
```

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
ggagaggagc gcctgttgtg gttgt                                            25

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
ttattccttc gcagataacc agtct                                            25

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9
tacggttaac cctttgaatc a                                                21

```
<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
gttacctggt taaactgtac t                                              21

<210> SEQ ID NO 11
<211> LENGTH: 38
<212> TYPE: DNA
<213> ORGANISM: Artificial sequence
<220> FEATURE:
<223> OTHER INFORMATION: Primer

<400> SEQUENCE: 11
atgcgtggca tgctgccgct tttcgagcct aagggacg                            38

<210> SEQ ID NO 12
<211> LENGTH: 42
<212> TYPE: DNA
<213> ORGANISM: Artificial sequence
<220> FEATURE:
<223> OTHER INFORMATION: Primer

<400> SEQUENCE: 12
ttccttcgca gataaccagt cttcccctat gccaacttcg ac                       42
```

HEAT-RESISTANT DNA POLYMERASE MUTANT WITH HIGH AMPLIFICATION ACTIVITY

TECHNICAL FIELD

The present invention belongs to the field of biotechnology. Specifically, the present invention relates to a heat-resistant DNA polymerase mutant with high amplification activity.

BACKGROUND

Taq enzyme is a heat-resistant DNA polymerase derived from a heat-resistant bacterium, *Thermus aquaticus*, with a molecular weight of 94 KDa, which has an optimal reaction temperature range of 75–80° C., an active half-life at 95° C. of 40 minutes and 5'-3'exonuclease activity in the presence of magnesium ions. Because of its resistance to high temperature, it is widely used in polymerase chain reaction (PCR) and is the enzyme of first choice for nucleic acid amplification and detection and other reactions. The commercial Taq enzyme is cloned and expressed using an *E. coli* prokaryotic expression system. Increasing sensitivity, accuracy, and durability of PCR reactions are required in modern molecular biological detection technology, and wild-type Taq enzyme cannot fulfill the requirement of practical applications. In order to make it more suitable for certain technologies, many attempts have been made in mutation of the Taq enzyme sequence, such as adding a DNA binding domain to obtain a stronger extension activity (Wang Y (2004). A novel strategy to engineer DNA polymerases for enhanced processivity and improved performance in vitro. Nucleic Acids Res 32, 1197-1207); site-directed mutagenesis and deletion of domains is performed to obtain a higher fidelity (Suzuki M, Yoshida S, Adman E T, Blank A, Loeb L A (2000) *Thermus Aquaticus* DNA polymerase I mutants with altered fidelity. Interacting mutations in the 0-Helix. J Biol Chem 275:32728-32735), a higher DNA polymerization activity (Mutant Taq DNA polymerases with improved elongation ability as a useful reagent for genetic engineering. Front Microbiol 5:461. doi: 10.3389/fmicb.2014.00461), tolerance to a high concentration of inhibitors (Zhang Z, Kermekchiev M B, Barnes W M (2010) Direct DNA amplification from crude clinical samples using a PCR enhancer cocktail and novel mutants of Taq. J Mol Diagn 12:152-161), a reduced 5'-3'exonuclease activity (Vainshtein I, Atrazhev A, Eom S H, Elliott J F, Wishart D S, Malcolm B A (1996) Peptide rescue of an N-Terminal truncation of the Stoffel fragment of Taq DNA polymerase. Protein Sci 5:51785-51792).

There are several ways to transform Taq enzyme. 1: Adding a domain to obtain a new property. For example, adding a single-stranded binding domain (SSB) or DNA binding protein Sso7 to enhance the binding of Taq enzyme to primers and template DNA, so that it has stronger extension ability and continuous synthesis ability, and is suitable for amplification reaction of long DNA fragments. However, adding a domain will directly increase the molecular weight of Taq enzyme, which may reduce the solubility and stability of Taq enzyme. Then the yield of prokaryotic expression production is reduced. 2: Removing non-essential domains on Taq enzyme. For example, the 5'-3'exonuclease domain (first 280 amino acids of N-terminus of Taq enzyme) is deleted, Taq enzyme only retains the active region of the nucleic acid polymerase, which reduces the possibility of degradation of primers and template DNA by a high concentration of Taq enzyme in order to achieve the purpose of improving the polymerization activity of Taq enzyme. However, the Taq enzyme mutant obtained from this method does not have 5'-3'exonuclease activity, so it is not suitable for quantitative PCR reaction based on the Taq man probe method, and the scope of application is limited. 3: Site-directed mutation method. Site-directed mutation is performed on the amino acids in the active site, magnesium ion binding site, and DNA binding site to increase the affinity of each site for substrates, templates, and primers, thereby improving tolerance to various inhibitors. Due to the complexity of protein structure, some amino acids far from the active site may also affect the overall structure of the enzyme. Therefore, it is difficult to modify the enzyme as a whole with mutation of only amino acids in certain active sites. Moreover, it is difficult to predict the effect of mutations at various sites on the overall structure with existing computer simulation technology. The workload of preparing mutants by site-directed mutation and screening mutants is very large, its efficiency is low, and some sites that significantly affect the activity cannot be identified.

SUMMARY OF INVENTION

The object of the present invention is to provide a heat-resistant DNA polymerase mutant with high amplification activity.

In the first aspect of the present invention, there is provided a mutated DNA polymerase that is mutated at one or more sites selected from the group consisting of: V453, F495, E507, K508, T509, A518, S624, Y672, E734, R737, F749, T757, L764, H785, wherein the amino acid residues are numbered based on SEQ ID NO. 2.

In another preferred example, the activity of the mutated DNA polymerase is at least 1.5 times, preferably at least 2 times; more preferably at least 3 times larger than that of wild-type DNA polymerase (SEQ ID NO: 2).

In another preferred example, the amino acid sequence of wild-type DNA polymerase is set forth in SEQ ID NO: 2.

In another preferred example, the amino acid sequence of the mutated DNA polymerase has at least 80% homology, more preferably at least 90% homology, most preferably at least 95% homology, such as at least 96%, 97%, 98%, 99% homology to SEQ ID NO: 2.

In another preferred example, the mutated DNA polymerase is selected from the group consisting of mutants 1-20:

| Mutant No. | Mutated amino acid |
| --- | --- |
| 1 | E507A, K508L, E734E, F749K |
| 2 | K508L, V453A, R737K |
| 3 | E734G |
| 4 | F749G, K508L, L764K |
| 5 | E507Q, T757S |
| 6 | H785G |
| 7 | S624T, F749V |
| 8 | E734F, F749V |
| 9 | K508L, R737W, Y672R |
| 10 | E507H, H785L |
| 11 | A518Q, E734M |
| 12 | F495R, F749T |
| 13 | K508L, F749T, E734F |
| 14 | R737P, S624K |
| 15 | T757W, V453G, E507M |
| 16 | F749E, H785G, F495G |
| 17 | E734F, Y672P |
| 18 | T509L, H785K |

-continued

| Mutant No. | Mutated amino acid |
|---|---|
| 19 | E734G, T757S, L764Q |
| 20 | K508L, V453A, A518Q |

In another preferred example, the number of mutation sites in the mutated DNA polymerase is 1-4, preferably 2 or 3.

In another preferred example, the mutated DNA polymerase is selected from each specific mutant enzyme listed in Table 2.

In another preferred example, the mutated DNA polymerase includes the mutation sites of each specific mutant enzyme listed in Table 2.

In another preferred example, the mutated DNA polymerase is mutated based on the wild-type DNA polymerase as set forth in SEQ ID NO: 2, and the mutated DNA polymerase includes a mutation site selected from the group consisting of:
  (1) E507A, K508L, E734E, F749K;
  (2) K508L, V453A, R737K
  (3) E734G
  (4) F749G, K508L, L764K
  (5) E507Q, T757S
  (6) H785G
  (7) S624T, F749V
  (8) E734F, F749V
  (9) K508L, R737W, Y672R
  (10) E507H, H785L
  (11) A518Q, E734M
  (12) F495R, F749T
  (13) K508L, F749T, E734F
  (14) R737P, S624K
  (15) T757W, V453G, E507M
  (16) F749E, H785G, F495G
  (17) E734F, Y672P
  (18) T509L, H785K
  (19) E734G, T757S, L764Q; and
  (20) K508L, V453A, A518Q.

In the second aspect of the present invention, there is provided a polynucleotide molecule encoding the mutated DNA polymerase according to the first aspect of the present invention.

In the third aspect of the present invention, there is provided a vector containing the nucleic acid molecule according to the second aspect of the present invention.

In the fourth aspect of the present invention, there is provided a host cell containing the vector according to the first aspect of the present invention or a chromosome integrated with the nucleic acid molecule according to the second aspect of the present invention.

In another preferred example, the host cell is a prokaryotic cell or an eukaryotic cell.

In another preferred example, the prokaryotic cell is *E. coli*.

In another preferred example, the eukaryotic cell is a yeast cell.

In the fifth aspect of the present invention, there is provided a method for preparing the mutated DNA polymerase according to the first aspect of the present invention, comprising the steps of:
  (i) culturing the host cell according to the fourth aspect of the present invention under suitable conditions to express the mutated DNA polymerase; and
  (ii) isolating the mutated DNA polymerase.

In another preferred example, the temperature for culturing the host cell in step (i) is 20° C.-40° C., preferably 25° C.-37° C., such as 35° C.

In the sixth aspect of the present invention, there is provided a kit comprising the mutated DNA polymerase according to the first aspect of the present invention.

It should be understood that, within the scope of the present invention, the above technical features of the present invention and the technical features specifically described below (e.g., in embodiments) can be combined with each other, thereby forming a new or preferred technical solution. As space is limited, not every technical solution will be illustrated herein.

DETAILED DESCRIPTION

After extensive and intensive research, the inventor has screened out a series of amino acid sites and mutations that play a key role in Taq enzyme amplification performance and polymerization performance, and has obtained Taq enzyme mutants with high amplification performance using protein directed evolution technology to construct a random mutation library for the polymerase active domain of Taq enzyme, and gradually applying screening pressure to eliminate unsuitable mutations naturally and to accumulate mutations with dominant traits. On this basis, the present invention has been completed.

Before describing the present invention, it should be understood that the present invention is not limited to the specific methods and experimental conditions, as such methods and conditions may vary. It should also be understood that the terminology as used herein is for the purpose of describing specific embodiments and is not intended to be limiting, and the scope of the present invention will be limited only by the appended claims.

Unless otherwise defined, all technical and scientific terms used herein have the same meaning as commonly understood by those skill in the art to which this invention belongs. As used herein, when used in reference to a recited value, the term "about" means that the value can vary from the recited value by no more than 1%. For example, as used herein, the expression "about 100" includes 99 and 101 and all values therebetween (e.g., 99.1, 99.2, 99.3, 99.4, etc.).

Although any methods and materials similar or equivalent to those described in the present invention can be used in the practice or testing of the present invention, the preferred methods and materials are exemplified herein.

Taq Enzyme

Taq enzyme is widely used in polymerase chain reaction (PCR) and is the enzyme of first choice for reactions such as nucleic acid amplification and detection. The commercial Taq enzyme is cloned and expressed using an *E. coli* prokaryotic expression system.

The DNA sequence of the wild-type Taq enzyme is as follows:

```
                                         (SEQ ID NO: 1)
ATGCGTGGCATGCTGCCGCTTTTCGAGCCTAAGGGACGCGTTCTTCT

TGTGGATGGACATCATCTGGCGTACCGTACCTTTCATGCCCTGAAGGGCC

TGACCACTTCGCGTGGGGAACCCGTGCAAGCAGTTTATGGATTCGCCAAA

TCGTTACTTAAGGCTCTGAAGGAGGATGGTGATGCGGTCATTGTTGTGTT

CGACGCAAAAGCTCCCTCGTTCCGTCACGAGGCCTACGGCGGCTATAAAG
```

-continued
```
CTGGGCGTGCACCCACACCTGAGGATTTTCCCCGGCAACTTGCTTTGATA
AAGGAATTAGTAGACCTGTTAGGCCTGGCGCGGTTAGAAGTGCCGGGTTA
CGAAGCAGATGACGTCTTGGCTAGTTTAGCGAAAAAGGCTGAAAAAGAG
GGATATGAAGTGCGGATCCTGACCGCGGATAAAGATCTGTATCAACTGTT
GTCCGACCGTATTCACGTGCTTCATCCGGAGGGCTACTTGATAACCCCGG
CTTGGCTGTGGGAGAAATATGGGCTGCGTCCAGATCAGTGGGCTGATTAT
CGTGCACTTACAGGCGATGAATCTGATAATCTTCCCGGCGTCAAGGGGAT
TGGTGAGAAAACCGCCCGTAAACTTTTGGAGGAGTGGGGCAGCTTGGAG
GCGCTGTTGAAGAATCTGGATCGTTTGAAACCCGCTATACGGGAAAAAT
CTTGGCGCACATGGACGACTTAAAACTGTCTTGGGACCTGGCGAAAGTTC
GTACTGATTTGCCGCTGGAGGTCGACTTTGCGAAGCGTCGCGAGCCCGAT
CGTGAACGTCTTCGCGCATTTCTGGAGCGTTTAGAATTTGGCTCCCGTTG
CATGAGTTTGGTTTGCTTGAAAGCCCGAAGGCACTTGAGGAAGCTCCTTG
GCCTCCGCCTGAGGGCGCTTTTGTCGGATTTGTCTTGAGCCGTAAAGAAC
CGATGTGGGCGGACTTACTGGCCCTTGCTGCTGCTCGTGGGGTCGCGTG
CATCGCGCACCGGAGCCATACAAAGCACTTCGTGACCTTAAAGAAGCCCG
TGGCTTGTTGGCAAAAGATTTAAGTGTCCTGGCTTTACGCGAGGGCTTGG
GCTTACCACCGGGAGATGATCCGATGCTTTTGGCCTATCTGCTGGACCCG
AGCAACACGACTCCAGAGGGCGTTGCCCGTCGTTATGGCGGAGAATGGA
CGGAGGAGGCGGGAGAGCGCGCAGCGTTAAGCGAGCGTCTGTTTGCTAA
TCTGTGGGGACGCTTAGAGGGAGAGGAGCGCCTGTTGTGGTTGTACCGTG
AAGTGGAACGGCCGCTGAGTGCAGTGTTAGCTCACATGGAAGCAACCGG
GGTGCGGCTGGACGTTGCGTATTTGCGTGCGCTGTCGTTAGAGGTCGCGG
AGGAAATAGCCCGTCTGGAGGCCGAAGTATTCCGTTTGGCTGGCCATCCT
TTCAACCTGAACAGTCGGGATCAGCTGGAACGTGTACTTTTTGATGAACT
GGGGCTGCCCGCCATCGGCAAAACCGAAAAAACCGGCAAACGTAGCACC
TCTGCGGCAGTGCTGGAAGCGTTACGTGAAGCTCATCCGATTGTGGAGAA
AATTCTGCAATATCGCGAATTGACGAAACTGAAGAGCACCTATATTGATC
CGCTGCCAGACTTAATTCACCCCCGTACCGGACGGTTGCATACCCGCTTC
AACCAGACCGCGACGGCGACAGGGCGGCTGAGTAGCAGCGATCCGAACC
TGCAAAACATTCCCGTGCGTACCCCGCTGGGTCAGCGTATTCGCCGTGCT
TTCATTGCCGAGGAAGGCTGGCTGCTGGTCGCGCTGGACTACTCGCAAAT
CGAATTGCGTGTGTTGGCCCACCTGTCGGGCGACGAAAACTTAATACGCG
TGTTTCAAGAAGGTCGTGACATACATACTGAAACCGCGTCCTGGATGTTT
GGAGTCCCACGGGAGGCTGTCGATCCTCTTATGCGTCGTGCCGCCAAAAC
AATTAACTTCGGAGTTCTGTACGGCATGTCGGCACATCGTTTATCACAGG
AACTGGCGATTCCGTATGAAGAAGCGCAGGCCTTCATAGAACGTTATTTC
CAATCATTCCCCAAGGTGCGGGCCTGGATTGAGAAGACCCTGGAAGAGG
GCCGTCGTCGTGGCTATGTAGAGACTCTGTTCGGACGTCGGCGGTATGTA
CCCGATCTTGAGGCCCGTGTGAAGTCCGTTCGTGAGGCAGCAGAACTAT
GGCGTTTAACATGCCAGTCCAGGGCACAGCGGCGGACCTGATGAAATTA
```

-continued
```
GCTATGGTTAAGCTGTTTCCGCGTTTGGAAGAAATGGGCGCTCGTATGCT
GTTACAGGTTCATGACGAGTTAGTATTAGAAGCACCGAAGGAGCGTGCCG
AAGCCGTGGCCCGGTTAGCCAAAGAGGTAATGGAAGGCGTCTACCCCCTT
GCAGTCCCGCTTGAAGTCGAAGTTGGCATAGGGGAAGACTGGTTATCTGC
GAAGGAA
```

The amino acid sequence of the wild-type Taq enzyme is as follows:

(SEQ ID NO: 2)
```
MRGMLPLFEPKGRVLLVDGHHLAYRTFHALKGLTTSRGEPVQAVYGFAK
SLLKALKEDGDAVIVVFDAKAPSFRHEAYGGYKAGRAPTPEDFPRQLAL
IKELVDLLGLARLEVPGYEADDVLASLAKKAEKEGYEVRILTADKDLYQ
LLSDRIHVLHPEGYLITPAWLWEKYGLRPDQWADYRALTGDESDNLPGV
KGIGEKTARKLLEEWGSLEALLKNLDRLKPAIREKILAHMDDLKLSWDL
AKVRTDLPLEVDFAKRREPDRERLRAFLERLEFGSLLHEFGLLESPKAL
EEAPWPPPEGAFVGFVLSRKEPMWADLLALAAARGGRVHRAPEPYKALR
DLKEARGLLAKDLSVLALREGLGLPPGDDPMLLAYLLDPSNTTPEGVAR
RYGGEWTEEAGERAALSERLFANLWGRLEGEERLLWLYREVERPLSAVL
AHMEATGVRLDVAYLRALSLEVAEEIARLEAEVFRLAGHPFNLNSRDQL
ERVLFDELGLPAIGKTEKTGKRSTSAAVLEALREAHPIVEKILQYRELT
KLKSTYIDPLPDLIHPRTGRLHTRFNQTATATGRLSSSDPNLQNIPVRT
PLGQRIRRAFIAEEGWLLVALDYSQIELRVLAHLSGDENLIRVFQEGRD
IHTETASWMFGVPREAVDPLMRRAAKTINFGVLYGMSAHRLSQELAIPY
EEAQAFIERYFQSFPKVRAWIEKTLEEGRRRGYVETLFGRRRYVPDLEA
RVKSVREAAERMAFNMPVQGTAADLMKLAMVKLFPRLEEMGARMLLQVH
DELVLEAPKERAEAVARLAKEVMEGVYPLAVPLEVEVGIGEDWLSAKE
```

The amino acid positions and mutation modes that are highly related to Taq enzyme amplification activity are identified through directed evolution in the present invention. Related mutated amino acid sites include: V453, F495, E507, K508, T509, A518, S624, Y672, E734, R737, F749, T757, L764, and H785, and the amino acid residues are numbered based on SEQ ID NO: 2. Mutation of the above amino acid position to any other amino acid may produce a Taq enzyme mutant with higher activity. Preferred mutant form includes: E507A/Q/H/M, K508L, E734G/F/M, F749K/G/V/T/E, L764K/Q, V453A/G, R737K/W/P, T757S/W, H785G/L/K, S624T/K, Y672R/P, A518Q, F495G/R, T509L.

The amino acid sites and mutation modes thereof highly related to Taq enzyme activity are screened from a random mutation library with directed evolution technology in the present invention. The number of mutants is $10^5$ times more than that of the site-directed mutation, which is more conducive to identify the mutation sites with synergistic effects that cannot be predicted by existing computer simulation techniques. Furthermore, based on the principle of directed evolution, the accumulated dominant traits are those most suitable for the added screening conditions, so the mutants obtained are certainly the optimal individuals among all mutants.

In a preferred embodiment of the present invention, the activity of the mutant DNA polymerase provided by the present invention is at least 1.2 times, preferably at least 1.3 times, more preferably at least 1.5 times, such as more than 2 times higher than that of the wild-type DNA polymerase (SEQ ID NO: 2).

In a preferred embodiment of the present invention, the method of assaying the activity of the mutated DNA polymerase and wild-type DNA polymerase (SEQ ID NO: 2) is as follows:

| | |
|---|---|
| PCR reaction solution: pET28a vector | 100 pg |
| Taq enzyme mutant or wild-type Taq enzyme | 10 ng |
| 10XTaq enzyme reaction solution (100 mM Tris, 500 mM KCl, 100 mM $(NH_4)_2SO_4$, pH 8.0) | 2 ul |
| pET28_F primer | 4 pmol |
| pET28_R primer | 4 pmol |
| dNTPs (2.5 mM) | 2 uL |
| $ddH_2O$ | added to 20 ul |
| PCR program: 95° C. for 5 minutes, 30 cycles (95° C. for 15 seconds, 55° C. for 15 seconds, 72° C. for 10 seconds), 4° C. ∞ | |

The PCR product was purified by ethanol precipitation, the light absorption of the product was measured at 260 nm, and the total amount of PCR product (ng) corresponding to each cycle was calculated.

Wherein, the following pair of primers was used in the PCR reaction:

```
pET28_F primer:
                            (SEQ ID NO: 9)
TACGGTTAACCCTTTGAATCA pET28_R primer:
                            (SEQ ID NO: 10)
GTTACCTGGTTAAACTGTACT.
```

Dividing the total amount of PCR products obtained using Taq enzyme mutants by the total amount of PCR products obtained using wild-type Taq enzymes is the activity multiple of Taq enzyme mutants compared to wild-type Taq enzymes.

Those skilled in the art can use conventional methods to obtain the sequence of the Taq enzyme gene of the present invention, for example, by complete artificial synthesis or PCR synthesis. A preferred method of synthesis is asymmetric PCR. The method of asymmetric PCR uses a pair of primers of unequal amounts to produce a large amount of single-stranded DNA (ssDNA) after PCR amplification. This pair of primers are called unrestricted primer and restricted primer, respectively, and their ratio is generally 50-100:1. In the first 10-15 cycles of the PCR reaction, the amplification product is mainly double-stranded DNA, but when the restricted primer (low concentration primer) is depleted, the PCR guided by the unrestricted primer (high concentration primer) will produce a large amount of single-stranded DNA. The primers used in PCR can be appropriately selected according to the sequence information of the present invention disclosed herein, and can be synthesized by conventional methods. The amplified DNA/RNA fragments can be separated and purified by conventional methods such as gel electrophoresis.

The Taq enzyme of the present invention can be expressed or produced by conventional recombinant DNA technology, comprising the steps of:

(1) Transforming or transducing a suitable host cell with a polynucleotide encoding the protein of the present invention, or with a recombinant expression vector containing the polynucleotide;
(2) Culturing the host cell in a suitable culture medium;
(3) Isolating and purifying the protein of interest from the culture medium or cell to obtain the Taq enzyme.

Methods well known by those skilled in the art can be used to construct an expression vector containing the DNA sequence encoding the Taq enzyme of the present invention and suitable transcription/translation control signals, preferably a commercially available vector, pET28. These methods include in vitro recombinant DNA technology, DNA synthesis technology, in vivo recombinant technology, etc. The DNA sequence can be effectively linked to an appropriate promoter in an expression vector to guide mRNA synthesis. The expression vector also includes a ribosome binding site for translation initiation and a transcription terminator. In addition, the expression vector preferably contains one or more selectable marker genes to provide a phenotypic trait for selection of transformed host cells.

The recombinant vector includes in the 5' to 3' direction: a promoter, a gene of interest and a terminator. If desired, the recombinant vector may also include the following elements: a protein purification tag, 3' polynucleotide signal, an untranslated nucleic acid sequence, a transporting and targeting nucleic acid sequence, a selection marker (antibiotic resistance gene, fluorescent protein, etc.), an enhancer, or an operator.

Methods for preparing recombinant vectors are well known to those skill in the art. The expression vector may be a bacterial plasmid, bacteriophage, yeast plasmid, plant cell virus, mammalian cell virus, or other vector. To sum up, any plasmid and vector can be used as long as it is able to replicate and stabilize in a host.

Those skilled in the art can construct a vector containing the promoter of the present invention and/or the gene sequence of interest using well-known methods. These methods comprise in vitro recombinant DNA technology, DNA synthesis technology, in vivo recombinant technology etc.

The expression vector of the present invention can be used to transform an appropriate host cell so that the host transcribes the target RNA or expresses the target protein. The host cell may be a prokaryotic cell, such as *E. coli, Corynebacterium glutamicum, Brevibacterium flavum, Streptomyces, Agrobacterium*; or a lower eukaryotic cell, such as a yeast cell; or a higher eukaryotic cell, such as a plant cell. Those skilled in the art know how to select appropriate vectors and host cells. Transformation of host cells with recombinant DNA can be performed using conventional techniques well known to those skilled in the art. When the host is a prokaryote (such as *E. coli*), it can be treated with $CaCl_2$) method or electroporation. When the host is a eukaryote, the following DNA transfection methods can be used: calcium phosphate co-precipitation method, conventional mechanical methods (such as microinjection, electroporation, liposome packaging, etc.). The plant can also be transformed using methods such as *Agrobacterium* transformation or gene gun transformation, such as leaf disc method, immature embryo transformation method, flower bud soaking method, etc. The transformed plant cells, tissues or organs can be regenerated into plants using conventional methods to obtain transgenic plants.

Term "operably linked" means that the target gene to be transcribed for expression is linked to its control sequence in a manner conventional in the art for expression.

Culturing of Engineering Bacteria and Fermentation Production of Target Protein

After obtaining the engineered cells, the engineered cells can be cultured under suitable conditions to express the protein encoded by the gene sequence of the present invention. Depending on the host cell, the culture medium used in the culture can be selected from a variety of conventional media and cultured under conditions suitable for the growth of the host cell. When the host cell grows to an appropriate cell density, the selected promoter is induced by an appropriate method (such as temperature conversion or chemical induction), and the cell is cultured for another period of time.

In the present invention, conventional fermentation conditions can be used. Representative conditions comprise (but are not limited to):
(a) Regarding temperature, the fermentation and induction temperature of Taq enzyme is maintained at 25-37° C.;
(b) Regarding pH during the induction period, the pH during the induction period is controlled at 3-9;
(c) Regarding dissolved oxygen (DO), DO is controlled at 10-90%, and the maintenance of dissolved oxygen can be achieved by the input of oxygen/air mixed gas;
(d) Regarding the supplements, the type of the supplements should preferably include carbon sources such as glycerin, methanol, and glucose, which can be supplemented alone or mixed;
(e) Regarding IPTG concentration during the induction period, conventional induction concentrations can be used in the present invention, usually the IPTG concentration is controlled at 0.1-1.5 mM;
(f) Regarding the induction time, without any particular limitation, it is usually 2-20 hours, preferably 5-15 hours.

The target protein Taq enzyme of the present invention is present within *E. coli* cells, the host cells are collected by a centrifuge, and then the host cells are crushed by high-pressure, mechanical force, enzymatic hydrolysis or other cell disruption methods, preferably the high-pressure method to release recombinant proteins. The host cell lysate can be preliminarily purified by methods such as flocculation, salting out, and ultrafiltration, and then purified by chromatography, ultrafiltration, etc., or can be directly purified by chromatography.

Chromatography techniques include cation exchange chromatography, anion exchange chromatography, gel filtration chromatography, hydrophobic chromatography, affinity chromatography, etc. Common chromatography methods comprise:

1. Anion Exchange Chromatography:

Anion exchange chromatography media include (but are not limited to): Q-Sepharose®, DEAE-Sepharose®. If the salt concentration of the fermentation sample is high, which affects the binding to the ion exchange medium, the salt concentration needs to be reduced before ion exchange chromatography. The sample can be exchanged with an equilibration buffer by dilution, ultrafiltration, dialysis, gel filtration chromatography, etc. until it is similar to the corresponding ion exchange column equilibration solution system, and then the sample is loaded for gradient elution of salt concentration or pH.

2. Hydrophobic Chromatography:

Hydrophobic chromatography media include (but are not limited to): Phenyl-Sepharose™, Butyl-Sepharose™, Octyle-Sepharose™. The salt concentration of the sample is increased by adding NaCl, $(NH_4)_2SO_4$, etc., then the sample is loaded, and eluted by reducing the salt concentration. heteroproteins with large differences in hydrophobicity is removed by hydrophobic chromatography.

3. Gel Filtration Chromatography

Hydrophobic chromatography media include (but are not limited to): Sephacryl®, Superdex™, Sephadex®. The buffer system is exchanged by gel filtration chromatography, or it is further purified.

4. Affinity Chromatography

Affinity chromatography media include (but are not limited to): HiTrap™ HeparinHPColumns.

5. Membrane Filtration

Ultrafiltration media include: organic membranes such as polysulfone membranes, inorganic membranes such as ceramic membranes, and metal membranes. The purpose of purification and concentration may be achieved with membrane filtration.

The Advantages of the Present Invention are (1) The heat-resistant DNA polymerase mutant with high amplification activity of the present invention has a significant increase in the amount of products from amplification at the same number of PCR cycles as the wild-type Taq enzyme.
(2) The heat-resistant DNA polymerase mutant with high amplification activity of the present invention can produce the same amount of product from amplification in a shorter time under the same conditions as the wild-type Taq enzyme, thereby increasing the efficiency of detection.

The present invention will be further described in detail below in conjunction with specific examples. It should be understood that these examples are only used to illustrate the present invention and not to limit the scope of the present invention. The experimental methods without detailed conditions in the following examples are generally in accordance with conventional conditions such as those described in Sambrook. J et al. "Guide to Molecular Cloning Laboratory" (translated by Huang Peitang et al., Beijing: Science Press, 2002), or in accordance with the conditions recommended by the manufacturer. Unless otherwise illustrated, percentages and parts are calculated by weight. The experimental materials and reagents used in the following examples can be obtained commercially unless otherwise illustrated.

Example 1: Construction of Random Mutant Plasmid of Taq Enzyme

The DNA sequence of polymerase active domain of Taq enzyme (coding sequence of amino acids 423-831) was amplified by low-fidelity PCR (Error-PCR) with a mutation rate of 0.3%, and then the remaining coding sequence (sequence of amino acids 1-423) was ligated and cloned into pET28a prokaryotic expression vector to obtain a random mutant plasmid of Taq enzyme. Specific steps were as follows:

1) Using Taq-pET28a plasmid as a template, and designing primer T (1-423) to amplify the Taq (1-423) fragment.

Taq (1-423) DNA Seq (SEQ ID NO: 3)
ATGCGTGGCATGCTGCCGCTTTTCGAGCCTAAGGGACGCGTTCTTCT

TGTGGATGGACATCATCTGGCGTACCGTACCTTTCATGCCCTGAAGGGCC

-continued

TGACCACTTCGCGTGGGGAACCCGTGCAAGCAGTTTATGGATTCGCCAAA

TCGTTACTTAAGGCTCTGAAGGAGGATGGTGATGCGGTCATTGTTGTGTT

CGACGCAAAAGCTCCCTCGTTCCGTCACGAGGCCTACGGCGGCTATAAAG

CTGGGCGTGCACCCACACCTGAGGATTTTCCCCGGCAACTTGCTTTGATA

AAGGAATTAGTAGACCTGTTAGGCCTGGCGCGGTTAGAAGTGCCGGGTTA

CGAAGCAGATGACGTCTTGGCTAGTTTAGCGAAAAAGGCTGAAAAAGAG

GGATATGAAGTGCGGATCCTGACCGCGGATAAAGATCTGTATCAACTGTT

GTCCGACCGTATTCACGTGCTTCATCCGGAGGGCTACTTGATAACCCCGG

CTTGGCTGTGGGAGAAATATGGGCTGCGTCCAGATCAGTGGGCTGATTAT

CGTGCACTTACAGGCGATGAATCTGATAATCTTCCCGGCGTCAAGGGGAT

TGGTGAGAAAACCGCCCGTAAACTTTTGGAGGAGTGGGGCAGCTTGGAGG

CGCTGTTGAAGAATCTGGATCGTTTGAAACCCGCTATACGGGAAAAAATC

TTGGCGCACATGGACGACTTAAAACTGTCTTGGGACCTGGCGAAAGTTCG

TACTGATTTGCCGCTGGAGGTCGACTTTGCGAAGCGTCGCGAGCCCGATC

GTGAACGTCTTCGCGCATTTCTGGAGCGTTTAGAATTTGGCTCCCTGTTG

CATGAGTTTGGTTTGCTTGAAAGCCCGAAGGCACTTGAGGAAGCTCCTTG

GCCTCCGCCTGAGGGCGCTTTTGTCGGATTTGTCTTGAGCCGTAAAGAAC

CGATGTGGGCGGACTTACTGGCCCTTGCTGCTGCTCGTGGGGGTCGCGTG

CATCGCGCACCGGAGCCATACAAAGCACTTCGTGACCTTAAAGAAGCCCG

TGGCTTGTTGGCAAAAGATTTAAGTGTCCTGGCTTTACGCGAGGGCTTGG

GCTTACCACCGGGAGATGATCCGATGCTTTTGGCCTATCTGCTGGACCCG

AGCAACACGACTCCAGAGGGCGTTGCCCGTCGTTATGGCGGAGAATGGA

CGGAGGAGGCGGGAGAGCGCGCAGCGTTAAGCGAGCGTCTGTTTGCTAA

TCTGTGGGGACGCTTAGAGGGAGAG

T1-423_PF:
(SEQ ID NO.: 4)
5' ATATCATATGCGTGGCATGCTGCCGCTTTT 3'

T1-423_PR:
(SEQ ID NO.: 5)
5' GCATGAATTCCGTCTCCTCTCCCTCTAAGC 3'

PCR Reaction System and Program:

| | |
|---|---|
| plasmid Taq-pET28a | 10 ng |
| T1-423_PF primer | 4 pmol |
| T1-423_PR primer | 4 pmol |
| 2.5 mM dNTP | 2 ul |
| 10X reaction buffer | 2 ul |
| KAPA HiFi DNA Polymerase | 5 U |
| ddH2O | added to total volume of 20 ul |
| PCR program: 95° C. for 3 minutes, 25 cycles (95° C. for 30 seconds, 60° C. for 30 seconds, 72° C. for 1 minute), 72° C. for 3 minutes, storage at 4° C. | |

The PCR product was purified and recovered with DNA gel recovery kit, digested with NdeI and XhoI, and ligated into pET28a vector. The sequence was confirmed by sequencing to be correct, and the resulting plasmid was named as Taq (1-423)-pET28.

2) Using Taq-pET28a plasmid as a template, using Clontech Diversify® PCR Random Mutagenesis Kit (Takara Bio, Dalian, PT3393-2), and designing primers (TMu_F/R) to amplify Taq (423-822) fragments.

Taq (423-832) DNA Seq
(SEQ ID NO.: 6)
GGAGAGGAGCGCCTGTTGTGGTTGTACCGTGAAGTGGAACGGCCGC

TGAGTGCAGTGTTAGCTCACATGGAAGCAACCGGGGTGCGGCTGGACGTT

GCGTATTTGCGTGCGCTGTCGTTAGAGGTCGCGGAGGAAATAGCCCGTCT

GGAGGCCGAAGTATTCCGTTTGGCTGGCCATCCTTTCAACCTGAACAGTC

GGGATCAGCTGGAACGTGTACTTTTTGATGAACTGGGGCTGCCCGCCATC

GGCAAAACCGAAAAAACCGGCAAACGTAGCACCTCTGCGGCAGTGCTGG

AAGCGTTACGTGAAGCTCATCCGATTGTGGAGAAAATTCTGCAATATCGC

GAATTGACGAAACTGAAGAGCACCTATATTGATCCGCTGCCAGACTTAAT

TCACCCCCGTACCGGACGGTTGCATACCCGCTTCAACCAGACCGCGACGG

CGACAGGGCGGCTGAGTAGCAGCGATCCGAACCTGCAAAACATTCCCGT

GCGTACCCCGCTGGGTCAGCGTATTCGCCGTGCTTTCATTGCCGAGGAAG

GCTGGCTGCTGGTCGCGCTGGACTACTCGCAAATCGAATTGCGTGTGTTG

GCCCACCTGTCGGGCGACGAAAACTTAATACGCGTGTTTCAAGAAGGTCG

TGACATACATACTGAAACCGCGTCCTGGATGTTTGGAGTCCCACGGGAGG

CTGTCGATCCTCTTATGCGTCGTGCCGCCAAAACAATTAACTTCGGAGTT

CTGTACGGCATGTCGGCACATCGTTTATCACAGGAACTGGCGATTCCGTA

TGAAGAAGCGCAGGCCTTCATAGAACGTTATTTCCAATCATTCCCCAAGG

TGCGGGCCTGGATTGAGAAGACCCTGGAAGAGGGCCGTCGTCGTGGCTAT

GTAGAGACTCTGTTCGGACGTCGGCGGTATGTACCCGATCTTGAGGCCCG

TGTGAAGTCCGTTCGTGAGGCAGCAGAACGTATGGCGTTTAACATGCCAG

TCCAGGGCACAGCGGCGGACCTGATGAAATTAGCTATGGTTAAGCTGTTT

CCGCGTTTGGAAGAAATGGGCGCTCGTATGCTGTTACAGGTTCATGACGA

GTTAGTATTAGAAGCACCGAAGGAGCGTGCCGAAGCCGTGGCCCGGTTA

GCCAAAGAGGTAATGGAAGGCGTCTACCCCCTTGCAGTCCCGCTTGAAGT

CGAAGTTGGCATAGGGGAAGACTGGTTATCTGCGAAGGAATAA

TMu_F:
(SEQ ID NO.: 7)
5' GGAGAGGAGCGCCTGTTGTGGTTGT 3'

TMu_R:
(SEQ ID NO.: 8)
5' TTATTCCTTCGCAGATAACCAGTCT 3'

PCR reaction system and program:

| | |
|---|---|
| 10*Titanium Taq buffer | 5 ul |
| dGTP (2 mM) | 1 ul |
| 50* Diversify dNTP Mix | 1 ul |
| TMu_F primer | 10 pmol |
| TMu_R primer | 10 pmol |
| Titanium Taq | 1 ul |
| ddH2O | added to 50 ul |
| 95° C. for 3 minutes, 25 cycles (95° C. for 30 seconds, 60° C. for 30 seconds, 68° C. for 2 minutes), 68° C. for 5 minutes, storage for 4° C. | |

The PCR product was digested with BsmBI and XhoI, then ligated with Taq (1-423)-pET28 plasmid digested with BsmBI and XhoI, BL21 (DE3) expression host bacteria was transformed with the ligated product, and the number of transformants was counted.

Example 2: Expression and Directed Evolution Screening of Taq Enzyme Mutants BL21 (DE3) expression strain was transformed with the Taq enzyme mutant plasmid and induced to express Taq enzyme mutation library. The BL21 (DE3) induced expression bacteria containing Taq enzyme mutant library were dispersed and packaged by emulsion PCR system, and subjected to PCR reaction to amplify and obtain DNA containing Taq enzyme mutant fragments. Then, the DNA fragments produced from amplification by emulsion PCR were subjected to high-fidelity PCR secondary amplification using Taq enzyme-specific primers, and the amplified DNA products were re-cloned into the pET28a expression vector to complete a screening process. Then, the screening process of emulsion PCR-secondary high-fidelity PCR-cloning into pET28a expression vector was repeated, and the extension time of emulsion PCR in each screening was gradually shortened to accumulate mutant populations with high extension activity and high amplification activity. The specific steps were as follows:

1) The transformant obtained in Example 1 was taken and inoculated into LB medium, incubated at 37° C. for 6 hours with shaking, isopropylthiogalactoside (IPTG) was added to a final concentration of 0.1 mM, and incubated at 37° C. for 3 hours. The cells were collected by centrifugation, washed twice with ddH$_2$O, and finally resuspended with ddH$_2$O. The light absorption (OD600 value) of the cell solution was determined at 600 nm, and it was diluted to the final concentration of OD600=1.0 with ddH$_2$O.

2) Preparation of oil phase solution

| | |
|---|---|
| Tween-80 | 200 ul |
| Triton X-100 | 25 ul |
| Mineral oil | 10 ml |

The above three reagents were combined and mixed evenly.

3) Preparation of aqueous phase reaction solution

The cell resuspension solution prepared in step 1) with OD600=1.0 was diluted 100 times with ddH$_2$O to prepare the following reaction solution

| | |
|---|---|
| 10XTaq enzyme reaction solution (100 mM Tris, 500 mM KCl, 100 mM (NH$_4$)$_2$SO$_4$, pH 8.0) | 13 ul |
| BSA (100 mg/ml) | 26 uL |
| pET28_F primer | 10 pmol |
| pET28_R primer | 10 pmol |
| dNTPs (2.5 mM) | 26 uL |
| Diluted cell resuspension solution | 26 ul |
| dd H$_2$O | added to 260 ul |

```
pET28_F primer:
                            (SEQ ID NO.: 9)
TACGGTTAACCCTTTGAATCA pET28_R primer:
                            (SEQ ID NO.: 10)
GTTACCTGGTTAAACTGTACT
```

4) Preparation of emulsion system 200 ul of aqueous phase+400 ul of oil phase were taken and mixed in a 2 ml tube, shaked at high speed for 10 minutes on a vortex shaker. 5 of PCR tubes were taken, each was filled with 100 ul of mixed solution. PCR program: 95° C. for 5 minutes, 25 cycles (95° C. for 30 seconds, 55° C. for 30 seconds, 72° C. for 2 minutes), 72° C. for 5 minutes, 4° C. ∞

5) The emulsion PCR product was transferred to a 1.5 ml tube, with 166 ul of water-saturated ether added, vortexed for 30 seconds, centrifuged at 12000 rpm for 10 minutes, and the lower liquid phase was removed, allowed to stand at room temperature for 10 minutes until the ether volatilized. The liquid product was extracted with phenol-chloroform method, and then recovered by ethanol precipitation overnight.

6) High-fidelity PCR secondary amplification products

The product of step 4) was used as a template for secondary PCR amplification

| | |
|---|---|
| The product of step 4) | 2 ul |
| Taq_F primer | 4 pmol |
| Taq_R primer | 4 pmol |
| dd H$_2$O | 6 ul |
| KAPA HiFi mix | 10 ul |
| PCR program: 95° C. for 5 minutes, 20 cycles (95° C. for 30 seconds, 62° C. for 30 seconds, 72° C. for 2 minutes), 72° C. for 5 minutes, 4° C. ∞ | |

```
Taq_F primer:
                            (SEQ ID NO.: 11)
ATGCGTGGCATGCTGCCGCTTTTCGAGCCTAAGGGACG Taq_R primer:
                            (SEQ ID NO.: 12)
TTCCTTCGCAGATAACCAGTCTTCCCCTATGCCAACTTCGAC
```

7) The PCR product was purified with DNA product purification recovery kit, and then relinked to pET28a expression vector. So far, one round of screening was completed.

8) Steps (1)-(6) were repeated for the transformants relinked to pET28a vector, the conditions of emulsion PCR was changed according to the program in the table below, and selection pressure was gradually added to the mutation library.

The second round of screening: 95° C. for 5 minutes, 25 cycles (95° C. for 30 seconds, 55° C. for 30 seconds, 72° C. for 1.5 minutes), 72° C. for 5 minutes, 4° C. ∞

The third round of screening: 95° C. for 5 minutes, 20 cycles (95° C. for 30 seconds, 55° C. for 30 seconds, 72° C. for 1.5 minutes), 72° C. for 5 minutes, 4° C. ∞

The fourth round of screening: 95° C. for 5 minutes, 15 cycles (95° C. for 30 seconds, 55° C. for 30 seconds, 72° C. for 30 seconds), 72° C. for 5 minutes, 4° C. ∞

After 4 rounds of screening, the resulting Taq enzyme mutant transformants were used in the high-throughput screening of Example 3.

Example 3: High-Throughput Screening of Taq Enzyme Mutants 384 clones were randomly picked out from the mutation library obtained in Example 2, after culturing and inducing for expression, their amplification activity was tested by high-throughput PCR reaction, and 20 mutants with high amplification activity were selected among them. The detailed steps were as follows:

1) 384 single clones were selected, inoculated into LB medium, incubated at 37° C. for 6 hours, with isopropylthiogalactoside (IPTG) added at a final concentration of 0.1 mM, and incubated at 37° C. for 3 hours.
2) The cells after induction culture were collected by centrifugation, with lysate containing 0.1 mg/ml lysozyme (50 Mm Tris, 50 Mm NaCl, 5% glycerol pH8.5) added. The cells were resuspended, incubated at 37° C. for 10 minutes, and heated at 75° C. for 30 minutes. Then they were centrifuged at 12000 rpm for 10 minutes, and the supernatant was taken.
3) A 96-well PCR plate was taken with the following reaction components added to each well:

| | |
|---|---|
| 10XTaq enzyme reaction solution (100 mM Tris, 500 mM KCl, 100 mM (NH$_4$)$_2$SO$_4$, pH 8.0) | 2 ul |
| pET28_F primer | 4 pmol |
| pET28_R primer | 4 pmol |
| dNTPs (2.5 mM) | 2 uL |
| Treated supernant | 1 ul |
| ddH$_2$O | added to 20 ul |
| PCR program: 95° C. for 5 minutes, 20 cycles (95° C. for 30 seconds, 62° C. for 30 seconds, 72° C. for 60 seconds), 4° C. ∞ | |

5 ul of the PCR product was subjected to agarose gel electrophoresis, the 20 clones with the highest yield were selected by comparing the yield of the PCR product in the supernatant prepared by each clone. The amplification yield of each mutant was 1.2 times to 2 times more than that of the wild-type.

Example 4: Confirmation of the Mutation Sites in the Dominant Taq Enzyme Mutant The DNA sequence of the Taq enzyme mutant selected in Example 3 was sequenced to determine the mutation in its amino acid sequence, and the high-frequency mutation sites and their mutation forms were counted.

TABLE 1

| Mutant No. | Mutated amino acid |
|---|---|
| 1 | E507A, K508L, E734E, F749K |
| 2 | K508L, V453A, R737K |
| 3 | E734G |
| 4 | F749G, K508L, L764K |
| 5 | E507Q, T757S |
| 6 | H785G |
| 7 | S624T, F749V |
| 8 | E734F, F749V |
| 9 | K508L, R737W, Y672R |
| 10 | E507H, H785L |
| 11 | A518Q, E734M |
| 12 | F495R, F749T |
| 13 | K508L, F749T, E734F |
| 14 | R737P, S624K |
| 15 | T757W, V453G, E507M |
| 16 | F749E, H785G, F495G |
| 17 | E734F, Y672P |
| 18 | T509L, H785K |
| 19 | E734G, T757S, L764Q |
| 20 | K508L, V453A, A518Q |

The 20 mutants with better amplification activity were sequenced, and their amino acid mutations were counted as shown in the above table. V453, F495, E507, K508, T509, A518, S624, Y672, E734, R737, F749, T757, L764, and H785 were repeated at high frequency in 20 mutants, proving that these mutations had a significant effect on the amplification activity of Taq enzyme.

Example 5: Comparison of Mutated Taq Enzyme and Wild-Type Taq Enzyme

The Taq enzyme mutants were taken, and after expression and purification, the following amplification test was performed with wild-type Taq enzyme:

| | |
|---|---|
| pET28a vector | 100 pg |
| Taq enzyme mutant/Wild-type Taq enzyme | 10 ng |
| 10XTaq enzyme reaction solution (100 mM Tris, 500 mM KCl, 100 mM (NH$_4$)$_2$SO$_4$, pH 8.0) | 2 ul |
| pET28_F primer | 4 pmol |
| pET28_R primer | 4 pmol |
| dNTPs (2.5 mM) | 2 uL |
| ddH$_2$O | added to 20 ul |
| PCR program: 95° C. for 5 minutes, n cycles (95° C. for 15 seconds, 55° C. for 15 seconds, 72° C. for 10 seconds), 4° C. ∞ | |

The above reaction solutions were prepared, PCR amplification was performed for 15, 20, 25, 30 cycles, precipitated with ethanol to purify the PCR products. The light absorption of the products at 260 nm was measured, and the total amount of PCR products (ng) corresponding to each cycle number was thereby calculated. The results were as follows:

TABLE 2

| | Number of PCR amplification cycles | | | |
|---|---|---|---|---|
| Taq enzyme | 15 | 20 | 25 | 30 |
| Taq enzyme mutant 1 | 104.35 | 604.25 | 1124.31 | 1643.24 |
| Taq enzyme mutant 2 | 61.89 | 412.58 | 701.39 | 981.95 |
| Taq enzyme mutant 3 | 74.07 | 493.80 | 839.46 | 1175.25 |
| Taq enzyme mutant 4 | 80.41 | 536.04 | 911.26 | 1275.76 |
| Taq enzyme mutant 5 | 65.30 | 435.33 | 740.05 | 1036.08 |
| Taq enzyme mutant 6 | 83.82 | 558.78 | 949.92 | 1329.89 |
| Taq enzyme mutant 7 | 59.45 | 396.34 | 673.78 | 943.29 |
| Taq enzyme mutant 8 | 55.55 | 370.35 | 629.60 | 881.44 |
| Taq enzyme mutant 9 | 66.27 | 441.82 | 751.10 | 1051.54 |
| Taq enzyme mutant 10 | 76.51 | 510.05 | 867.08 | 1213.91 |
| Taq enzyme mutant 11 | 72.61 | 484.06 | 822.90 | 1152.05 |
| Taq enzyme mutant 12 | 84.79 | 565.27 | 960.97 | 1345.35 |
| Taq enzyme mutant 13 | 78.94 | 526.29 | 894.69 | 1252.57 |
| Taq enzyme mutant 14 | 71.63 | 477.56 | 811.75 | 1136.59 |
| Taq enzyme mutant 15 | 62.86 | 419.08 | 712.44 | 997.42 |
| Taq enzyme mutant 16 | 63.35 | 422.33 | 717.96 | 1005.15 |
| Taq enzyme mutant 17 | 86.74 | 578.27 | 983.06 | 1376.28 |
| Taq enzyme mutant 18 | 53.60 | 357.36 | 607.51 | 850.51 |
| Taq enzyme mutant 19 | 68.22 | 454.82 | 773.19 | 1082.47 |
| Taq enzyme mutant 20 | 85.28 | 568.52 | 966.49 | 1353.08 |
| Wild-type Taq enzyme | 52.43 | 324.87 | 527.64 | 649.21 |

From the above results, it can be seen that the amount of products amplified by Taq enzyme mutants 1 to 20 at the same number of PCR cycles is significantly higher than that of wild-type Taq enzyme. Wherein, the amount of product obtained when mutant 1 was amplified for 20 cycles was already equivalent to that obtained by wild-type Taq enzyme for 30 cycles of amplification; under the same 30 amplification cycles, the amount of product obtained by mutant 1 is 2.5 times more than that of wild-type Taq enzyme.

Example 6: Use of Mutated Taq Enzyme in a Novel Coronavirus SARS-CoV-2 Fluorescent Quantitative PCR Detection Kit The Taq enzyme mutants 1 #, 6 #, and 17 # were selected, and the reaction system was prepared according to the table below

| | |
|---|---|
| NC (ORF1ab/N) PCR reaction solution A | 17 ul |
| Taq enzyme mutant/wild-type Taq enzyme | 10 ng |
| MMLV reverse transcriptase | 200 U |
| RNase Inhibitor | 20 U |
| NC(ORF1ab/N) positive quality control nucleic acid extract | 5 ul |

Wherein NC (ORF1ab/N) PCR reaction solution A, nucleic acid extract of NC (ORF 1 ab/N) positive quality control were both provided from 2019 Novel Coronavirus (2019-nCoV) ORF1ab N nucleic acid detection kit (PCR-fluorescent probe method) (Sun Yat-sen University, Daan Gene Co., Ltd.). MMLV reverse transcriptase and RNase Inhibitor are both prepared by Sun Yat-sen University, Daan Gene Co., Ltd. PCR program was set as follows:

| Step | Number of cycles | Temperature (° C.) | Running time | Fluorescent data acquisition |
|---|---|---|---|---|
| 1 | 1 | 50 | 00:15:00 | |
| 2 | 1 | 95 | 00:15:00 | |
| 3 | 45 | 94 | 00:00:15 | |
| | | 55 | 00:00:45 | ✓ |

The ct values of NC (ORF1ab/N) positive quality control with different concentration gradients amplified by each Taq enzyme mutant and wild-type Taq enzyme were as follows:

| | Concentration of NC(ORF1ab/N) positive quality control (copies/ml) | | | |
|---|---|---|---|---|
| | $10^6$ | $10^5$ | $10^4$ | $10^3$ |
| Taq enzyme mutant 1 | 22.5 | 25.16 | 28.24 | 31.54 |
| Taq enzyme mutant 6 | 23.14 | 26.41 | 29.55 | 33.01 |
| Taq enzyme mutant 17 | 24.09 | 27.65 | 30.97 | 34.52 |
| Wild-type Taq enzyme | 25.61 | 28.97 | 31.26 | 34.97 |

From the above results, it can be seen that the performance of Taq enzyme mutants on SARS-CoV-2 fluorescent quantitative PCR detection kit is significantly improved compared to the wild-type Taq enzyme.

All documents mentioned in the present invention are cited as references in this application, just as each document is individually cited as a reference. In addition, it should be understood that, after reading the above content of the present invention, those skilled in the art can make various changes or modifications to the present invention, and these equivalent forms also fall within the scope defined by the appended claims of the present application.

The invention claimed is:

1. A mutated DNA polymerase,
wherein the mutated DNA polymerase is mutated based on the wild-type DNA polymerase as set forth in SEQ ID NO: 2,
wherein the amino acid sequence of the mutated DNA polymerase has at least 98% homology to SEQ ID NO: 2, and the mutated DNA polymerase comprises the mutations:
F495R and F749T (Mutant No. 12).

2. A method for preparing the mutated DNA polymerase of claim 1, wherein the method comprises the steps of:
   (i) culturing a host cell under suitable conditions to express the mutant DNA polymerase; and
   (ii) isolating the mutated DNA polymerase,
wherein the host cell contains a chromosome integrated with the nucleic acid molecule encoding the mutated DNA polymerase of claim 1.

3. A kit, wherein the kit comprises the mutated DNA polymerase of claim 1.

* * * * *